US006908478B2

(12) United States Patent
Alferness et al.

(10) Patent No.: US 6,908,478 B2
(45) Date of Patent: Jun. 21, 2005

(54) ANCHOR AND PULL MITRAL VALVE DEVICE AND METHOD

(75) Inventors: Clifton A. Alferness, Redmond, WA (US); John M. Adams, Sammamish, WA (US); Mark L. Mathis, Kirkland, WA (US); David G. Reuter, Bothell, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 0 days.

(21) Appl. No.: 10/011,867

(22) Filed: Dec. 5, 2001

(65) Prior Publication Data

US 2003/0105520 A1 Jun. 5, 2003

(51) Int. Cl.⁷ .................................................. A61F 2/06
(52) U.S. Cl. ..................... 623/1.11; 623/2.36; 623/2.37; 606/108
(58) Field of Search ............................... 623/11.11, 1.1, 623/1.11, 1.12, 1.15, 1.16, 1.18, 1.2, 2.1, 2.11, 2.36, 2.37, 1.23, 2.38, 12, 66.1; 606/108, 198, 191–192, 194–195; 600/16, 37; 128/898

(56) References Cited

U.S. PATENT DOCUMENTS

| | | | |
|---|---|---|---|
| 4,055,861 | A | 11/1977 | Carpentier et al. |
| 4,164,046 | A | 8/1979 | Cooley |
| 4,485,816 | A | 12/1984 | Krumme |
| 4,550,870 | A | 11/1985 | Krumme et al. |
| 4,830,023 | A | 5/1989 | de Toledo et al. |
| 5,061,277 | A | 10/1991 | Carpentier et al. |
| 5,250,071 | A | 10/1993 | Palermo |
| 5,261,916 | A | 11/1993 | Engelson |
| 5,265,601 | A | 11/1993 | Mehra |
| 5,350,420 | A | 9/1994 | Cosgrove et al. |

(Continued)

FOREIGN PATENT DOCUMENTS

| | | |
|---|---|---|
| WO | WO 00/44313 A1 | 8/2000 |
| WO | WO 00/60995 A3 | 10/2000 |
| WO | WO 01/00111 A1 | 1/2001 |
| WO | WO 01/50958 A1 | 7/2001 |
| WO | WO 01/54618 | 8/2001 |
| WO | WO-2001/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO-2002/96275 A2 | 12/2002 |
| WO | WO-2003/15611 A2 | 2/2003 |
| WO | WO 03/049647 A1 | 6/2003 |

OTHER PUBLICATIONS

International Search Report for PCT/US02/15237, dated Apr. 18, 2003.

*Primary Examiner*—David J. Isabella
*Assistant Examiner*—Urmi Chattopadhyay
(74) *Attorney, Agent, or Firm*—Wilson Sonsini Goodrich & Rosati

(57) ABSTRACT

A device, system, and method effects mitral valve annulus geometry of a heart. The device includes a first anchor configured to be positioned within and fixed to the coronary sinus of the heart adjacent the mitral valve annulus within the heart. A cable is fixed to the first anchor and extends proximately therefrom and slidingly through a second anchor which is positioned and fixed in the heart proximal to the first anchor. A lock locks the cable to the second anchor when tension is applied to the cable for effecting the mitral valve annulus geometry.

21 Claims, 3 Drawing Sheets

U.S. PATENT DOCUMENTS

| | | |
|---|---|---|
| 5,514,161 A | 5/1996 | Limousin |
| 5,554,177 A | 9/1996 | Kieval et al. |
| 5,562,698 A | 10/1996 | Parker |
| 5,584,867 A | 12/1996 | Limousin |
| 5,601,600 A | 2/1997 | Ton |
| 5,733,325 A | 3/1998 | Robinson et al. |
| 5,824,071 A | 10/1998 | Nelson et al. |
| 5,891,193 A | 4/1999 | Robinson et al. |
| 5,895,391 A | 4/1999 | Farnholtz |
| 5,908,404 A | 6/1999 | Elliott |
| 5,935,161 A | 8/1999 | Robinson et al. |
| 5,961,545 A | 10/1999 | Lentz et al. |
| 5,984,944 A | 11/1999 | Forber |
| 6,027,517 A | 2/2000 | Crocker et al. |
| 6,077,295 A | 6/2000 | Limon et al. |
| 6,077,297 A | 6/2000 | Robinson et al. |
| 6,099,549 A | 8/2000 | Bosma et al. |
| 6,099,552 A | 8/2000 | Adams |
| 6,129,755 A | 10/2000 | Mathis et al. |
| 6,190,406 B1 | 2/2001 | Duerig et al. |
| 6,210,432 B1 | 4/2001 | Solem et al. |
| 6,275,730 B1 | 8/2001 | KenKnight et al. |
| 6,342,067 B1 | 1/2002 | Mathis et al. |
| 6,352,553 B1 | 3/2002 | van der Burg et al. |
| 6,352,561 B1 | 3/2002 | Leopold et al. |
| 6,395,017 B1 | 5/2002 | Dwyer et al. |
| 6,402,781 B1 | 6/2002 | Langberg et al. |
| 6,419,696 B1 | 7/2002 | Ortiz et al. |
| 6,442,427 B1 | 8/2002 | Boute et al. |
| 6,503,271 B2 | 1/2003 | Duerig et al. |
| 6,537,314 B2 | 3/2003 | Langberg et al. |
| 6,569,198 B1 | 5/2003 | Wilson et al. |
| 6,589,208 B2 | 7/2003 | Ewers et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,656,221 B2 | 12/2003 | Taylor et al. |
| 2001/0018611 A1 | 8/2001 | Solem et al. |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0035361 A1 | 3/2002 | Houser et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0103532 A1 | 8/2002 | Langberg et al. |
| 2002/0103533 A1 | 8/2002 | Langberg et al. |
| 2002/0138044 A1 | 9/2002 | Streeter et al. |
| 2002/0151961 A1 * | 10/2002 | Lashinski et al. ......... 623/1.15 |
| 2002/0169502 A1 * | 11/2002 | Mathis ...................... 623/2.11 |
| 2002/0169504 A1 * | 11/2002 | Alferness et al. ......... 623/2.36 |
| 2002/0183835 A1 | 12/2002 | Taylor et al. |
| 2002/0183836 A1 | 12/2002 | Liddicoat et al. |
| 2002/0183837 A1 * | 12/2002 | Streeter et al. ............ 623/2.11 |
| 2002/0183838 A1 | 12/2002 | Liddicoat et al. |
| 2002/0183841 A1 | 12/2002 | Cohn et al. |
| 2003/0018358 A1 | 1/2003 | Saadat |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0088305 A1 * | 5/2003 | Van Schie et al. ......... 623/1.12 |
| 2003/0130730 A1 | 7/2003 | Cohn et al. |
| 2003/0135267 A1 | 7/2003 | Solem et al. |

* cited by examiner under treatment, problems that do arise may be easily corrected with traditional open heart surgery.

ANCHOR AND PULL MITRAL VALVE DEVICE AND METHOD

FIELD OF THE INVENTION

The present invention generally relates to a device and method for treating dilated cardiomyopathy of a heart. The present invention more particularly relates to a device and method for reshaping the mitral valve annulus.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a comprised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously effect the geometry of the mitral valve annulus.

The device includes a resilient member having a cross sectional dimension for being received within the coronary sinus of the heart and a longitudinal dimension having an unstressed arched configuration when placed in the coronary sinus. The device partially encircles and exerts an inward pressure on the mitral valve. The inward pressure constricts the mitral valve annulus, or at least a portion of it, to essentially restore the mitral valve geometry. This promotes effective valve sealing action and eliminates mitral regurgitation.

The device may be implanted in the coronary sinus using only percutaneous techniques similar to the techniques used to implant cardiac leads such as pacemaker leads. One proposed system for implanting the device includes an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of resilient material, it conforms to the curvatures of the lumen as it is advanced through the sheath. The sheath is then partially retracted to permit the device to assume its unstressed arched configuration. Once the device is properly positioned, the introducer is then decoupled from the device and retracted through the sheath. The procedure is then completed by the retraction of the sheath. As a result, the device is left within the coronary sinus to exert the inward pressure on the mitral valve to restore mitral valve geometry.

The foregoing therapy has many advantages over the traditional open heart surgery approach. Since the device, system and method may be employed in a comparatively noninvasive procedure, mitral valve regurgitation may be treated at an early stage in the mitral regurgitation progression. Further, the device may be placed with relative ease by any minimally invasive cardiologist. Still further, since the heart remains completely intact throughout the procedure, the effectiveness of the procedure may be readily determined. Moreover, should adjustments be deemed desirable, such adjustments may be made during the procedure and before the patient is sent to recovery.

Another approach to treat mitral regurgitation with a device in the coronary sinus is based upon the observation that the application of a localized force against a discrete portion of the mitral valve annulus can terminate mitral regurgitation. This suggests that mitral valve dilation may be localized and nonuniform. Hence, the device applies a force to one or more discrete portions of the atrial wall of the coronary sinus to provide localized mitral valve annulus reshaping instead of generalized reshaping of the mitral valve annulus. Such localized therapy would have all the benefits of the generalized therapy. In addition, a localized therapy device may be easier to implant and adjust. The present invention provides a still further alternative for treating mitral regurgitation with a device placed in the coronary sinus adjacent to the mitral valve annulus.

SUMMARY OF THE INVENTION

The present invention provides a device for effecting mitral valve annulus geometry of a heart. The device includes a first anchor configured to be positioned within and fixed to the coronary sinus of the heart adjacent the mitral valve annulus within the heart, a cable fixed to the first anchor and extending proximally from the first anchor within the heart, a second anchor configured to be positioned in and fixed in the heart proximal to the first anchor and arranged to slidingly receive the cable, and a lock that locks the cable on the second anchor. As a result, when the first and second anchors are fixed within the heart, the cable is drawn proximally, and the cable is locked on the second anchor, the geometry of the mitral valve is effected.

The second anchor may be configured to be positioned and fixed in the coronary sinus. Alternatively, the second anchor may be configured to be positioned and fixed in the right atrium.

The first anchor may be self-expanding to fix the first anchor in the coronary sinus. Similarly, the second anchor may be self-expanding to fix the second anchor in the heart.

The second anchor may include the lock. The lock may include a ratchet. Further, the cable may include a coupling configured for releasable connection to a cable tension assembly.

The present invention further provides a device for effecting mitral valve annulus geometry in a heart including first anchor means for anchoring within the coronary sinus of the heart adjacent to the mitral valve annulus and second anchor means for anchoring within the heart proximal to the first anchor means. The device further includes cable means fixed to the first anchor means and extending proximally from the first anchor means, the cable means being slidably received by the second anchor means for spanning between the first and second anchor means, and lock means for locking the second anchor means to the cable means.

The present invention still further provides a method of effecting mitral valve annulus geometry in a heart. The method includes the steps of fixing a first anchor within the coronary sinus of the heart adjacent to the mitral valve annulus, anchoring a second anchor within the heart proximal to the first anchor, fixing a cable to the first anchor, the cable extending proximally from the first anchor and slidably through the second anchor, displacing the cable proximally relative to the second anchor to create tension in the cable, and locking the second anchor to the cable.

The present invention still further provides a system for effecting mitral valve annulus geometry. The system includes a mitral valve annulus device comprising a first anchor configured to be positioned within and fixed to the coronary sinus of the heart adjacent to mitral valve annulus within the heart, a cable fixed to the first anchor and extending proximally from the first anchor within the heart, a second anchor configured to be positioned and fixed in the heart proximal to the first anchor and arranged to slidingly receive the cable, and a lock that locks the cable on the second anchor. The system further includes a delivery assembly that deploys the mitral valve annulus device, the delivery assembly including a first push tool that engages the first anchor to position the first anchor within the coronary sinus, a second push tool that engages the second anchor to position the second anchor in the heart, and a tensioning member connectable to the cable that provides tension to the cable between the first and second anchors.

The present invention still further provides a method of effecting mitral valve geometry of a heart including the steps of advancing a guide catheter into the coronary sinus of the heart adjacent to the mitral valve annulus, pushing a self-deploying first anchor down and out of the guide catheter to deploy the first anchor in the coronary sinus adjacent to the mitral valve annulus, providing the first anchor with a cable extending proximally from the first anchor and through a second self-deploying anchor, and displacing the second self-deploying anchor down the guide catheter to a position proximal to the first anchor. The method further includes the steps of withdrawing the guide catheter while holding the second anchor to deploy the second anchor, pulling on the cable to create tension in the cable, and locking the cable to the second anchor.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, and the several figures of which like reference numerals identify identical elements, and wherein:

DETAILED DESCRIPTION OF THE INVENTION

Figure 1:
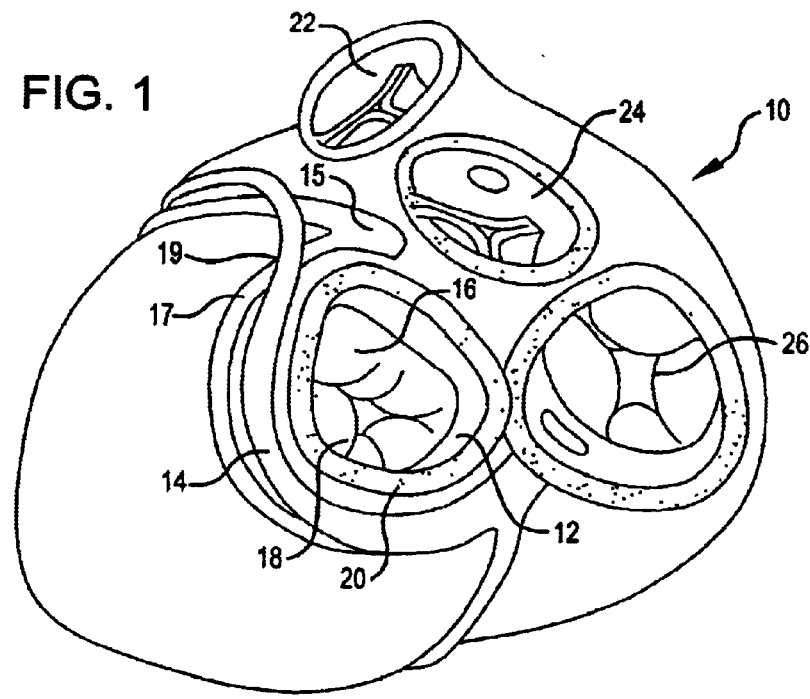
FIG. 1 is a superior view of a human heart with the atria removed.

Referring now to FIG. 1, it is a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy device of the present invention therein.

Figure 2:
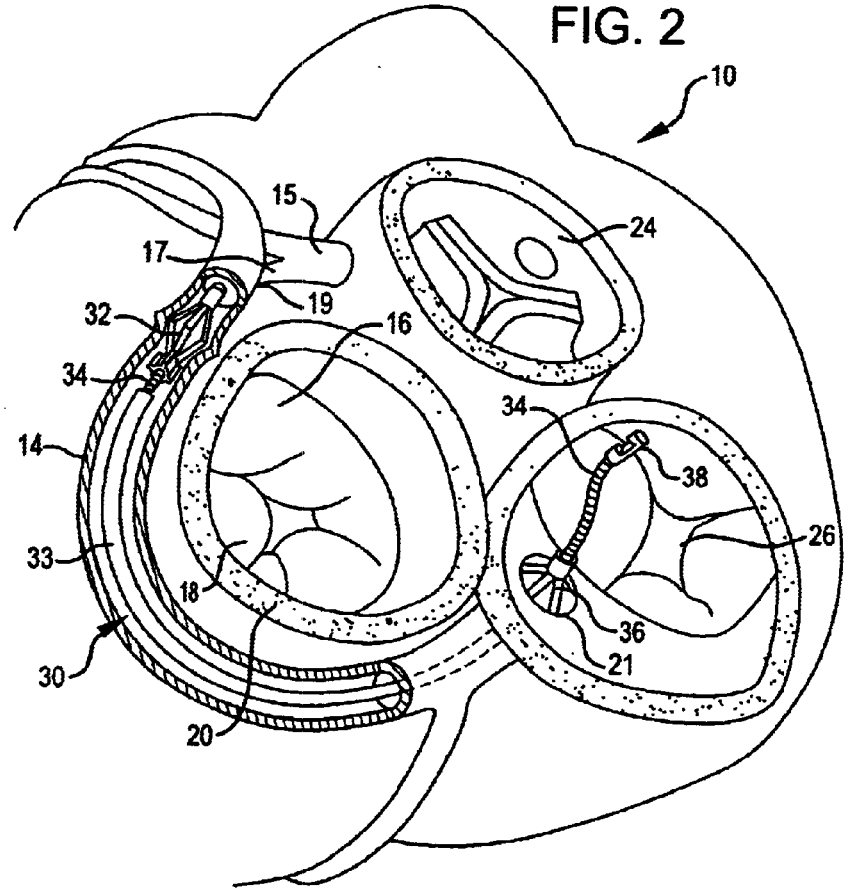
FIG. 2 is a superior view of a human heart similar to FIG. 1 illustrating a deployed mitral valve device embodying the present invention.

FIG. 2 shows a mitral valve therapy device 30 embodying the present invention. As may be noted in FIG. 2, the device 30 includes a first anchor 32, a cable 34, and a second anchor 36.

The first anchor 32 is located at the distal end of the device 30. The anchor 32 is self-expanding so as to be self-deployable when released in the coronary sinus 14. More specifically, the anchor 32 may be formed of a material such as Nitinol, a nickel/titanium alloy of the type well known in the art having shape memory. The anchor 32 has a toggle bolt-like configuration which expands when released to engage the inner wall of the coronary sinus 14 for anchoring or fixing the anchor 32 therein. Preferably, the anchor 32 is positioned just proximally to the crossover point 19 of the coronary sinus 14 and a circumflex artery 17.

The cable 34, which may be a single wire, a multi-stranded wire, a polymer cable or a Nitinol cable, is fixed to the first anchor 32 and extends proximally therefrom. The cable extends through the second anchor 36 which is positioned proximally from the first anchor 32. Here it will be noted that the second anchor is positioned within the coronary sinus just distal to the ostium 21 of the coronary sinus 14. The second anchor 36 may have a similar toggle bolt-like configuration and is also preferably self-expanding to be self-deployable.

The cable 34 terminates in a coupling 38. As may best be seen in FIG. 5, the coupling 38 is configured to releasably interlock with a corresponding coupling 40 carried by a tension cable 42.

Figure 5:
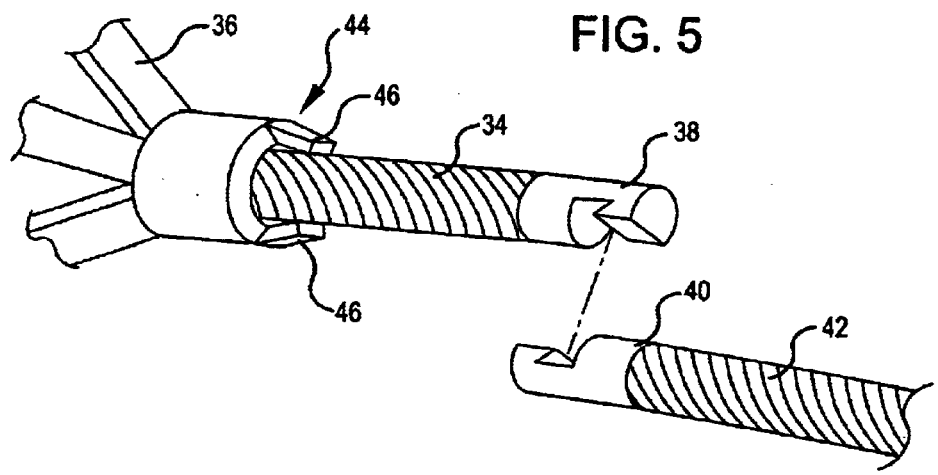
FIG. 5 is a perspective view illustrating details of the coupling and locking mechanisms employed in the device and assembly of FIGS. 3 and 4.

As may further be noted in FIG. 5, the second or proximal anchor 36 also includes a locking mechanism 44. Here, the locking mechanism 44 takes the form of a ratchet or ratchet-like mechanism 46 for locking the second anchor 36 to the cable 34.

When the device 30 is deployed as shown in FIG. 2, the first anchor 32 is fixed within the coronary sinus 14. The cable 34 extends proximally from the anchor 32 and slidably through the second anchor 36. The second anchor 36 is then positioned in its desired location within the heart proximal to the first anchor 32 and permitted to self-expand for being anchored within the heart. Then, the tension cable is used to pull proximally on the cable while the second anchor 36 is preferably held in its fixed position. Once a desired amount of tension is applied to the cable, the ratchet positively and permanently locks the cable 34 to the second anchor 36. With the cable 34 now under tension, the geometry of the mitral valve annulus 20 is now advantageously effected. The tension in the cable may be further adjusted while monitoring a parameter indicative of mitral regurgitation such as Doppler echo while adjusting the tension. The tension may be further adjusted by pushing the deployed proximal anchor 36 further down the cable 34 thereby shortening the distance between the proximal and the distal anchors. Once the proximal anchor position and proper cable tension is achieved, the tension cable assembly may be removed in a manner as more fully described hereinafter.

As will further be noted in FIG. 2, the cable 34 is provided with a covering 33. The covering 33 is preferably formed of a compressible material and serves to distribute forces of the cable applied against the inner wall of the coronary sinus 14. This force distribution precludes damage to the coronary sinus by the cable 34.

Figure 3:
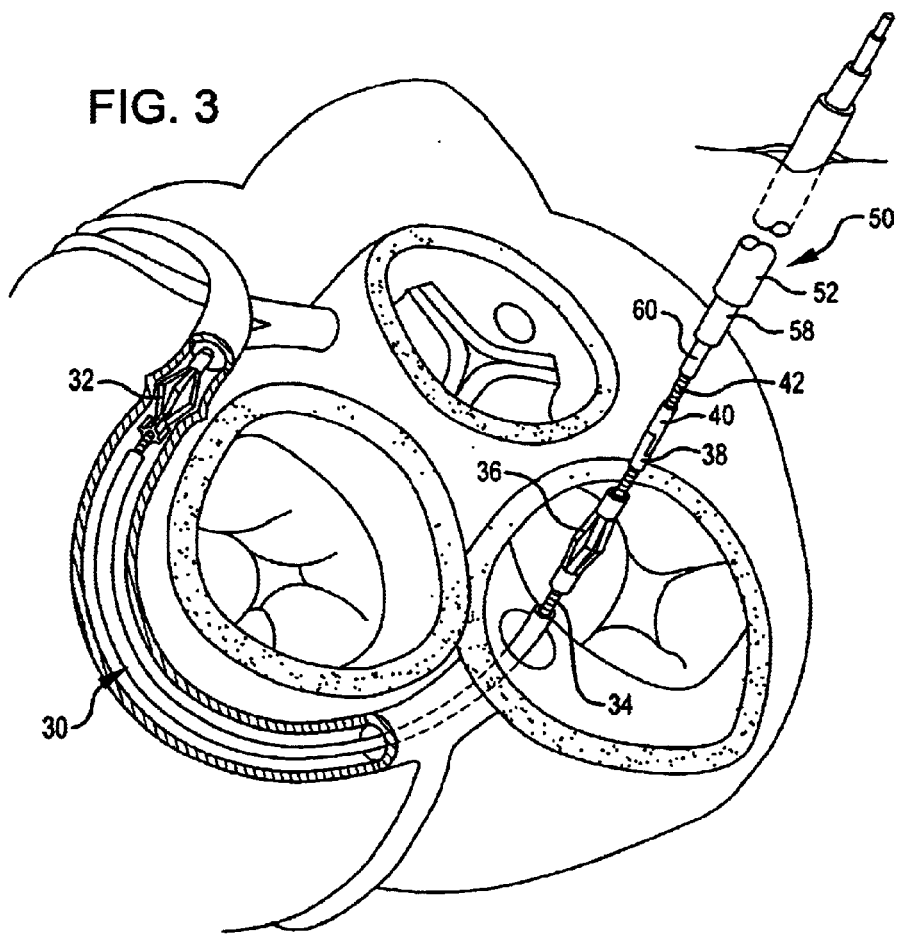
FIG. 3 is a superior view of a human heart similar to FIG. 2 illustrating an intermediate step in the deployment of the mitral valve device of FIG. 2 embodying the present invention.
Figure 4:
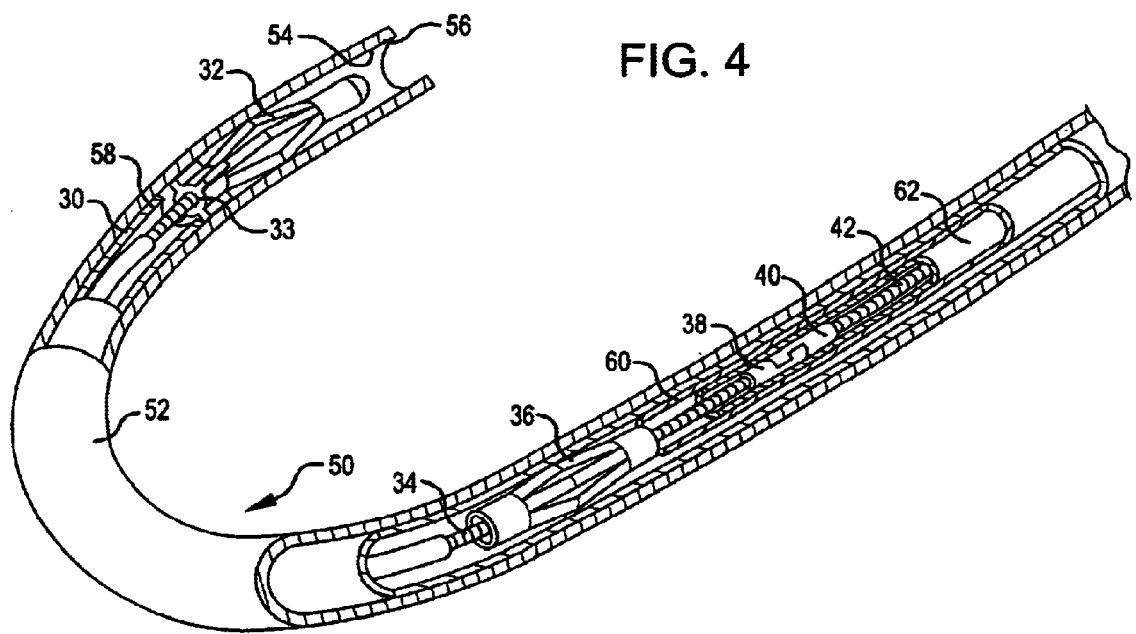
FIG. 4 is a perspective view with portions cut away of the device of FIG. 2 and a delivery assembly for deploying the device in accordance with an embodiment of the present invention.

FIGS. 3 and 4 show further details of the device 30 and its deployment assembly 50. As will be noted in FIG. 4, the deployment assembly 50 includes a catheter 52. The catheter 52 has a lumen 54 dimensioned for slidably receiving the device 30 in its predeployed state. The catheter 52 is advanced into the coronary sinus until its distal end 56 is at a desired position within the coronary sinus.

The assembly 50 further includes a first push tube 58 which engages a collar 33 of the first anchor 32. The push tube 58 may then be used to push the first anchor 32 to its desired position and out of the catheter 52 whereupon, the first anchor 32 self-expands for deployment. Once the first anchor 32 is fixed within the coronary sinus, the push tube 58 may then be removed.

The assembly 50 further includes a second push tube 60 coaxially arranged with the catheter 52 and first push tube 58 which may be fed down the catheter to engage the second anchor 36. The second push tube 60 is then used to push the second anchor 36 along the cable 34 to its desired position. Then, the catheter 52 is retracted to release the second anchor 36 to permit it to self-expand and be deployed.

The tension cable 42 is then coupled to the coupling 38 of the cable 34 and covered with a sheath 62 to maintain the coupling of the couplings 38 and 40. Tension is then applied to the cable 34 by proximally pulling on the tension cable 42 while the second push tube 60 holds the second anchor 36 stationary. When the desired tension is placed on the cable 34, further adjustment may be made as previously described. When this is completed, the first anchor 32 and the second anchor 36 are fixed in position with a tension in the cable 34. The catheter 52, the sheath 62, the second push tube 60, and the tension cable 42 may be removed to complete the deployment process.

Figure 6:
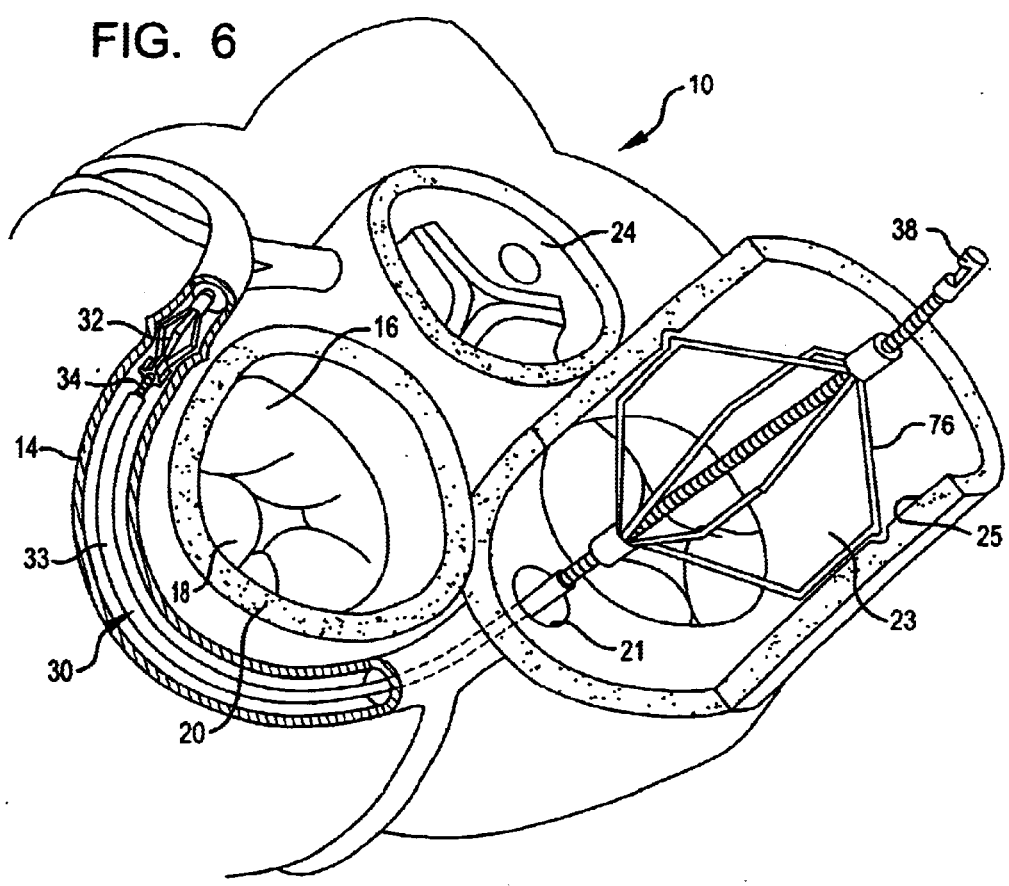
FIG. 6 is a further superior view of a human heart similar to that of FIG. 1 illustrating a further mitral valve device embodying the present invention.

FIG. 6 shows another mitral valve device 70 embodying the present invention. The device 70 is similar to the device 30 previously described except that its second or proximal anchor 76 is located and fixed within the right atrium 23 of the heart 10. To this end, the device 70 includes a first anchor 32, a cable 34, and a force distributor 33 as previously described. The second anchor 76 is configured so that when it self-expands, it engages the inner wall 25 of the right atrium 23 to hold it in place. In all other respects, the device 70 may be identical to the device 30.

While particular embodiments of the present invention have been shown and described, modifications may be made, and it is therefore intended in the appended claims to cover all such changes and modifications which fall within the true spirit and scope of the invention as defined by the appended claims.

What is claimed:

1. A system for effecting mitral valve annulus geometry comprising:
   a mitral valve annulus device comprising a first anchor configured to be positioned within and fixed to the coronary sinus of the heart adjacent to mitral valve annulus within the heart, a cable fixed to the first anchor and extending proximally from the first anchor within the heart, a second anchor configured to be positioned and fixed in the heart proximal to the first anchor and arranged to slidingly receive the cable, and a lock that locks the cable on the second anchor; and
   a delivery assembly that deploys the mitral valve annulus device, the delivery assembly including a first push tool that engages the first anchor to position the first anchor within the coronary sinus, a second push tool that engages the second anchor to position the second anchor in the heart, and a tensioning member connectable to the cable that provides tension to the cable between the first and second anchors.

2. The system of claim 1 wherein the delivery assembly further includes a guide catheter that guides the mitral valve annulus device into the coronary sinus.

3. The system of claim 2 wherein the first push tool comprises a first push tube.

4. The system of claim 3 wherein the second push tool comprises a second push tube.

5. The system of claim 4 wherein the guide catheter, the first push tube and the second push tube are coaxially arranged.

6. The system of claim 1 further including a releasable coupling that connects the cable of the device to the tensioning member.

7. The system of claim 6 wherein the tensioning member is a tensioning cable.

8. The system of claim 1 wherein the second anchor is configured to be positioned and fixed in the coronary sinus.

9. The system of claim 1 wherein the second anchor is configured to be positioned and fixed in the right atrium.

10. The system of claim 1 wherein the first anchor is self-expanding to fix the first anchor in the coronary sinus.

11. The system of claim 1 wherein the second anchor is self-expanding to fix the second anchor in the heart.

12. The system of claim 1 wherein the cable includes a pressure distributor.

13. The system of claim 1 wherein the second anchor includes the lock.

14. The system of claim 13 wherein the lock includes a ratchet.

15. A method of effecting mitral valve geometry of a heart, the method including the steps of:
   advancing a guide catheter into the coronary sinus of the heart adjacent to the mitral valve annulus;
   pushing a self-deploying first anchor down and out of the guide catheter to deploy the first anchor in the coronary sinus adjacent to the mitral valve annulus;
   providing the first anchor with a cable extending proximally from the first anchor and through a second self-deploying anchor;
   displacing the second self-deploying anchor down the guide catheter to a position proximal to the first anchor;
   withdrawing the guide catheter while holding the second anchor to deploy the second anchor;
   pulling on the cable to create tension in the cable; and
   locking the cable to the second anchor.

16. The method of claim 15 wherein the pushing step includes the step of pushing the first anchor with a push tube dimensioned to slide within the guide catheter.

17. The method of claim 15 wherein the displacing step includes the step of pushing the second anchor along the cable with a second push tube dimensioned to slide within the guide catheter.

18. The method of claim 15 including the further step of releasably coupling the cable to a tension cable prior to the pulling step.

19. The method of claim 15 wherein the displacing step includes the step of deploying the second anchor in the coronary sinus.

20. The method of claim 15 wherein the displacing step includes the step of deploying the second anchor in the right atrium of the heart.

21. The method of claim 15 wherein the pushing step includes locating the first anchor proximally to the circumflex artery within the coronary sinus.

* * * * *